(12) United States Patent
McMahon

(10) Patent No.: US 6,296,616 B1
(45) Date of Patent: Oct. 2, 2001

(54) GUIDEWIRE WITH SHAPED INTERMEDIATE PORTION

(75) Inventor: James C. McMahon, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/518,499

(22) Filed: Mar. 3, 2000

Related U.S. Application Data

(63) Continuation of application No. 08/972,654, filed on Nov. 18, 1997.

(51) Int. Cl.[7] .................................... A61B 5/00
(52) U.S. Cl. ................................. 600/585; 604/523
(58) Field of Search ..................... 600/585, 433, 600/434; 604/523

(56) References Cited

U.S. PATENT DOCUMENTS

| | | | |
|---|---|---|---|
| 3,731,671 | 5/1973 | Mageoh | 128/2.05 R |
| 3,928,519 | 12/1975 | Kashiyama et al. | 264/40 |
| 4,080,706 | 3/1978 | Heilman et al. | 29/173 |
| 4,534,363 | 8/1985 | Gold | 128/772 |
| 4,538,622 | 9/1985 | Samson et al. | 128/772 |
| 4,724,846 | 2/1988 | Evans III | 128/772 |
| 4,748,986 | 6/1988 | Morrison et al. | 128/772 |
| 4,807,596 | 2/1989 | Hochberger et al. | 128/4 |
| 4,840,623 | 6/1989 | Quackenbush | 604/280 |
| 5,061,273 | 10/1991 | Yock | 606/194 |
| 5,095,915 | 3/1992 | Engelson | 128/772 |
| 5,135,503 | 8/1992 | Abrams | 604/164 |
| 5,147,317 | 9/1992 | Shank et al. | 604/164 |
| 5,341,818 | 8/1994 | Abrams et al. | 128/772 |
| 5,345,945 | 9/1994 | Hodgson et al. | 128/772 |
| 5,358,493 | 10/1994 | Schweich, Jr. et al. | 604/264 |
| 5,404,887 | 4/1995 | Prather | 128/772 |
| 5,497,785 | 3/1996 | Viera | 600/585 |
| 5,507,729 | 4/1996 | Lindenberg et al. | 604/170 |
| 5,516,336 | 5/1996 | McInnes et al. | 606/194 |
| 5,551,443 | 9/1996 | Sepetka et al. | 600/585 |
| 5,606,979 | 3/1997 | Hodgson | 128/772 |
| 5,827,201 | 10/1998 | Samson et al. | 600/585 |

FOREIGN PATENT DOCUMENTS

| | | |
|---|---|---|
| 0 377 453 A1 | 11/1990 | (EP) . |
| WO 89/10088 | 2/1989 | (WO) . |
| WO 92/14508 | 3/1992 | (WO) . |

*Primary Examiner*—Robert L. Nasser
*Assistant Examiner*—Pamela L Wingood
(74) *Attorney, Agent, or Firm*—Heller, Ehrman, White & McAuliffe

(57) ABSTRACT

A guidewire for advancing a medical device such as a catheter through a patient's body lumen which has an elongated core with proximal and distal core sections, a flexible tubular member such as a coil on the distal end and an intermediate portion, preferably formed at least in part by a polymeric sheath proximal to the coil having contact regions and recessed non-contact regions.

16 Claims, 2 Drawing Sheets

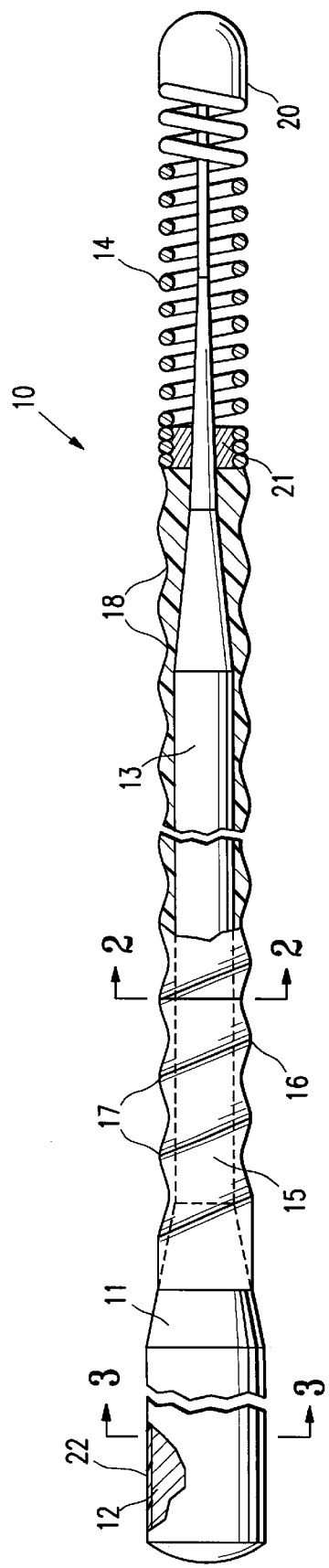
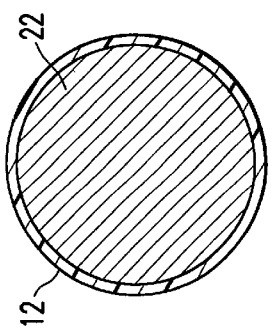
FIG. 1
FIG. 2
FIG. 3

GUIDEWIRE WITH SHAPED INTERMEDIATE PORTION

This is a continuation application of copending application Ser. No. 08/972,654 filed Nov.18, 1997, incorporated by reference.

BACKGROUND OF THE INVENTION

This invention relates to the field of guidewires for advancing intravascular devices such as stent delivery catheters, balloon dilatation catheters and atherectomy catheters within a body lumen Conventional guidewires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. A shapable member, which may be the distal extremity of the core member or a separate shaping ribbon which is secured to the distal extremity of the core member extends through the flexible body and is secured to the distal end of the flexible body by soldering, brazing or welding which forms a rounded distal tip. Torquing means are provided on the proximal end of the core member to rotate, and thereby steer, the guidewire while it is being advanced through a patient's vascular system.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); and U.S. Pat. No. 5,345,945 (Hodgson, et al.) which are hereby incorporated herein in their entirety by reference thereto.

In a typical coronary procedure using a guidewire, a guiding catheter having a preformed distal tip is percutaneously introduced into a patient's peripheral artery, e.g. femoral or brachial artery, by means of a conventional Seldinger technique and advanced and steered therein until the distal tip of the guiding catheter is seated in the ostium of a desired coronary artery.

There are two basic techniques for advancing a guidewire into the desired location within the patient's coronary anatomy through the in place guiding catheter. The first is a preload technique which is used primarily for over-the-wire (OTW) devices and the second is the bare wire technique which is used primarily for rail type systems.

With the preload technique, a guidewire is positioned within an inner lumen of an OTW device such as a dilatation catheter or stent delivery catheter with the distal tip of the guidewire just proximal to the distal tip of the catheter and then both are advanced through the guiding catheter to the distal end thereof. The guidewire is first advanced out of the distal end of the guiding catheter into the patient's coronary vasculature until the distal end of the guidewire crosses the arterial location where the interventional procedure is to be performed, e.g. a lesion to be dilated or a dilated region where a stent is to be deployed. The catheter, which is slidably mounted onto the guidewire, is advanced out of the guiding catheter into the patient's coronary anatomy over the previously introduced guidewire until the operative portion of the intravascular device, e.g. the balloon of a dilatation or a stent delivery catheter, is properly positioned across the arterial location. Once the catheter is in position with the operative means located within the desired arterial location, the interventional procedure is performed. The catheter can then be removed from the patient over the guidewire. Usually, the guidewire is left in place for a period of time after the procedure is completed to ensure reaccess to the arterial location is it is necessary. For example, in the event of arterial blockage due to dissected lining collapse, a rapid exchange type perfusion balloon catheter such as described and claimed in U.S. Pat. No. 5,516,336 (McInnes et al), can be advanced over the in-place guidewire so that the balloon can be inflated to open up the arterial passageway and allow blood to perfuse through the distal section of the catheter to a distal location until the dissection is reattached to the arterial wall by natural healing.

With the bare wire technique, the guidewire is first advanced by itself through the guiding catheter until the distal tip of the guidewire extends beyond the arterial location where the procedure is to be performed. Then a rail type catheter, such as described in U.S. Pat. No. 5,061,395 (Yock) and the previously discussed McInnes et al. which are incorporated herein by reference, is mounted onto the proximal portion of the guidewire which extends out of the proximal end of the guiding catheter which is outside of the patient. The catheter is advanced over the catheter, while the position of the guidewire is fixed, until the operative means on the rail type catheter is disposed within the arterial location where the procedure is to be performed. After the procedure the intravascular device may be withdrawn from the patient over the guidewire or the guidewire advanced further within the coronary anatomy for an additional procedure.

SUMMARY OF THE INVENTION

The present invention is directed to an improved guidewire having a flexible distal section which facilitates advancement through a patient's body lumen.

The guidewire of the present invention has an elongated core member with proximal and distal core sections with a flexible tubular member such as a helical coil is disposed about and secured to the distal part of the distal core section. The distal core section has one or more distally tapering segments. Proximal to the flexible tubular member, the guidewire has an exterior surface which is shaped to provide a plurality of contact regions and non-contact regions between adjacent contact regions.

In one presently preferred embodiment, the intermediate portion is defined by a sheath disposed about the core member and preferably formed of a polymeric material. The contact region or regions of the intermediate portion of the guidewire is generally about 20 to about 60% of the surface of the sheath. The outer diameter of the contact regions of the intermediate portion is preferably the same or approximately the same as the outer diameter of the flexible tubular member or coil on the distal part of the distal shaft section. However, if the flexible tubular member is of different outer diameter than the proximal core section, the intermediate portion may taper from the outer diameter of the proximal core section to the outer diameter of the coil. The distances between the peaks of the contact regions should be about 0.05 to about 5.0 mm, preferably about 0.1 to about 0.5 mm. The depth of the recessed non-contact regions may be about 0.01 to about 0.1 mm, preferably about 0.025 to about 0.075 mm as measured from the peaks of the contact regions. While the presently preferred intermediate portion of the guidewire having the contact and non-contact regions extends distally from the flexible tubular member and terminates distal to the proximal core section, the section having the contact and non-contact regions can extend proximally over most or all of the proximal core section.

By reducing the area of surface contact between the guidewire and a body lumen or a catheter lumen in which the guidewire is being moved relative thereto, the resistance to movement is greatly reduced. In one embodiment of the invention, solid or liquid lubricant can be maintained within recessed non-contact regions to further reduce frictional drag on the guidewire as it moves through a lumen or the frictional drag on a catheter as the catheter is moved over the intermediate portion of the guidewire. Pharmaceutical materials and diagnostic and therapeutic agents may also be incorporated into the recessed non-contact regions.

In one presently preferred embodiment of the invention, the intermediate guidewire portion having the contact and non-contact regions is defined by an intermediate sheath disposed about at least part of the distal guidewire section proximal to the flexible tubular member or coil on the distal part of the distal section.

These and other advantages of the invention will become more apparent from the following detailed description of the invention when taken in conjunction with the accompanying exemplary drawings.

BRIEF DESCRIPTION OF THE DRAWINGS

FIG. 1 is an elevational view partially in section of a guidewire embodying features of the invention wherein a sheath forming the intermediate portion has a helically shaped ridge.

FIG. 2 is a transverse cross-sectional view of the guidewire shown in FIG. 1 taken along the lines 2—2.

FIG. 3 is a transverse cross-sectional view of the guidewire shown in FIG. 1 taken along the lines 3—3.

DETAILED DESCRIPTION OF THE INVENTION

Figure 5:
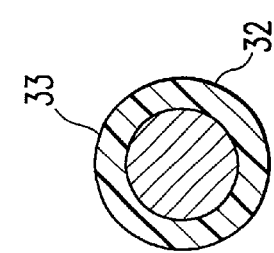
FIG. 5 is a transverse cross-sectional view of the embodiment shown in FIG. 4 taken along the lines 5—5.

FIGS. 1–3 depict a guidewire 10 embodying features of the invention which has an elongated core member 11 with a proximal core section 12, a distal core section 13 and a helical coil 14 on the distal extremity of the distal core section. An intermediate portion of the guidewire 10 proximal to the helical coil 14 is provided with a sheath 15, which is disposed about and secured to the distal core section 13, has an exterior surface 16 with contact regions 17 in the form of a helical ridge and a plurality of recessed (with respect to the contact regions) non-contact regions 18 disposed between adjacent contact regions. The peak-to-peak distance between the adjacent contact regions 17 is about 0.05 to about 5 mm, preferably about 0.1 to about 0.5 mm.

The distal end of coil 14 is secured to the distal tip of the distal core section 13 by suitable means, such as solder, a weldment, an adhesive, a body of polymeric material and the like which forms the rounded tip 20. The proximal end of the coil 14 is secured to the distal core section by solder 21. The proximal core section 12 has a polymeric jacket 22 which is preferably formed of lubricious polymeric materials such as fluoropolymers or hydrophilic materials. Other lubricious materials may be utilized.

Figure 4:
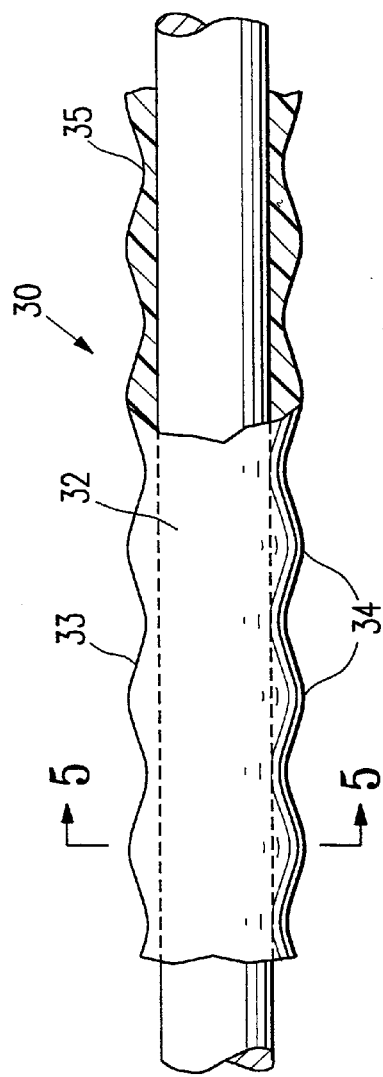
FIG. 4 is an elevational view partially in section of an alternative embodiment of the invention wherein a sheath on the intermediate portion has an undulating exterior surface.

An alternative embodiment of the invention is depicted in FIGS. 4 and 5 wherein the guidewire 30 has an intermediate portion proximal to the helical coil 31 covered with a sheath 32 which has an undulating exterior surface 33 with contact regions 34 in the form of a plurality of circular ridges and a plurality of recessed non-contact regions 35 between adjacent contact regions. The peak-to-peak distances between the contact surfaces 34 of this embodiment are the same or approximately the same as that for the contact regions 17 of the previously described embodiment.

Figure 7:
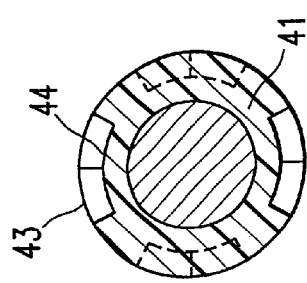
FIG. 7 is a transverse cross-sectional view of the embodiment shown in FIG. 6 taken along the lines 7—7.
Figure 6:
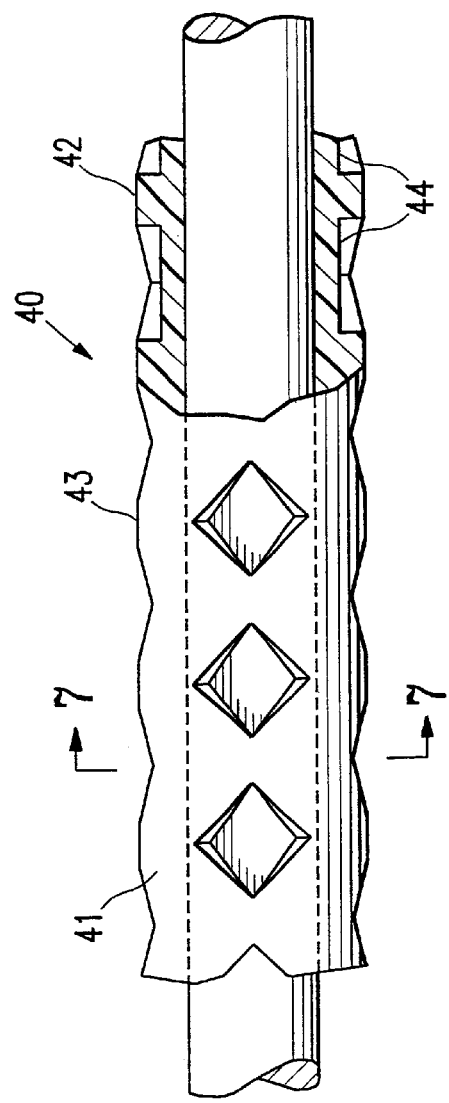
FIG. 6 is an elevational view partially in section of an alternative embodiment of the invention wherein the intermediate section has a closed figure design formed into the exterior surface thereof.

FIGS. 6 and 7 illustrate yet another alternative embodiment of the invention in which the guidewire 40 has an intermediate portion with a sheath 41 with a closed figure texture formed in the exterior surface 42 with contact regions 43 and recessed non-contact regions 44 for essentially the same purpose as the contact and non-contact regions of the previously discussed embodiments. The recessed non-contact regions may contain liquid or solid lubricant such as a fluoropolymer, a silicone coating such as MICROGLIDE™, or HYDROCOAT™. These recesses may also be employed as reservoirs for pharmaceutical materials, therapeutic agents or diagnostic agents.

The sheaths forming the intermediate portions of the guidewires of the present invention may be formed by first heat shrinking a thermoplastic polymeric material onto the distal core section proximal to the coil and then placing a clam-shell mold of the desired configuration about the heat shrunk material at elevated temperatures to shape the exterior of the intermediate sheath in the desired configuration. Other means may also be employed. For example, the exterior surface of a tubular polymeric member may first be formed into the desired shape and then the tubular member heat shrunk onto the distal core section. Other means including casting polymeric material about the distal core section into the desired shape. Machining polymeric material from the exterior of a tubular polymeric member on the distal core segment may also be employed to develop the contact and non-contact regions of the intermediate sheath. Suitable polymeric materials for the intermediate sheath include polyethylene, polyetheretherketone, polyvinyl chloride and polyurethane. A wide variety of other polymeric materials are contemplated. The sheathed intermediate portion of the guidewire is about 4 to about 38 cm in length, preferably about 6 to about 20 cm in length.

The guidewires of the invention may have typical guidewire dimensions. Guidewire length may generally be about 90 to about 300 cm, and for use within a patient's coronary anatomy commercially available guidewires are typically about 175 cm in length. Recently, however, longer guidewires, e.g. up to 190 cm in length, are being offered commercially by a variety of suppliers, including the present assignee. The proximal core section 12 may have a length of about 65 to about 280 cm, preferably about 150 to about 200 cm and a diameter generally about 0.008 to about 0.035 inch (0.20–0.89 mm), typically about 0.010 to about 0.020 inch (0.25–0.51 mm) for coronary artery uses. The distal core section is preferably much shorter than the proximal core section and generally is about 6 to about 40 cm, preferably about 8 to about 30 cm in length and tapers in the distal direction in one or more steps to smaller transverse dimensions.

The core member is preferably coated with a lubricous coating such as a fluoropolymer, e.g. TEFLON ® available from DuPont, which extends the length of the proximal core section 12. The distal section 13 is also provided a lubricous coating, not shown for purposes of clarity, such as a MICROGLIDE ™ coating used by the present assignee, Advanced Cardiovascular Systems, Inc. on many of its commercially available guidewires.

The tapered portion of the distal core segment is preferably followed distally with a manually shapable flattened core segment or shaping ribbon of about 1 to 4 cm in length which preferably has essentially constant transverse dimensions, e.g. 0.0005–0.002 inch (0.013–0.051 mm) by 0.002–0.006 inch (0.051–0.152 mm), typically about 0.001 by 0.003 inch (0.025–0.076 mm). A helical coil having transverse outer dimensions about the same as or slightly less than the proximal core section is secured by its distal end to the flattened distal tip of the core member, e.g. by means of solder, and by its proximal end at an intermediate position on the tapered distal core segment so that the distal end of the tapered core segment resides within the interior of the coil. The helical coil 14 may be formed all or in part of stainless steel, a suitable radiopaque material such as platinum or alloys thereof or other material such as stainless steel coated with a radiopaque material such as gold. The wire from which the coil is made generally has a transverse diameter of about 0.0015 to about 0.003 inch (0.04–0.08 mm) for coronary applications and up to 0.07 inch (0.18 mm) for peripheral applications. The overall length of the coil 14 is about 2 to about 15 cm, preferably about 2 about 6 cm. Multiple turns of the coil 14 may be expanded to provide additional flexibility.

Unless otherwise described herein, conventional materials and manufacturing methods may be used to make the guiding members of the present invention. Additionally, various modifications may be made to the present invention without departing from the scope thereof. Although individual features of embodiments of the invention may be shown in some of the drawings and not in others, those skilled in the art will recognize that individual features of one embodiment of the invention can be combined with any or all the features of another embodiment.

What is claimed is:

1. A guidewire for intralumenal advancement of a medical device within a patient, comprising:
    a) an elongated metallic core member which has a proximal core section and a distal core section;
    b) a flexible body which is disposed about and secured to a portion of the distal core section; and
    c) an intermediate non-metallic sheath which is disposed at a location proximal to the flexible body and which has an exterior with a plurality of contact regions and recessed non-contact regions disposed between contact regions.

2. The guidewire of claim 1 wherein the contact regions form a helical ridge on the exterior of the intermediate sheath which encircles the core member at least one time.

3. The guidewire of claim 1 wherein the contact regions form a plurality of circular ridges on the exterior of the intermediate sheath which are disposed about the core member.

4. The guidewire of claim 1 wherein the intermediate sheath has a closed figure texture formed in the exterior of the sheath with the contact regions surrounding non-contact regions.

5. The guidewire of claim 1 wherein recessed non-contact regions are configured to hold at least one component selected from the group consisting of a lubricant, a therapeutic agent and a diagnostic agent.

6. The guidewire of claim 1 wherein the non-metallic sheath is formed of a polymeric material.

7. The guidewire of claim 6 wherein the polymeric material is a heat shrunk thermoplastic.

8. The guidewire of claim 1 wherein the contact regions comprise about 20 to about 60% of the surface of the intermediate sheath.

9. The guidewire of claim 1 wherein the contact regions are spaced about 0.05 to about 5 mm.

10. The guidewire of claim 1 wherein the contact regions are spaced about 0.1 to about 0.5 mm.

11. The guidewire of claim 1 wherein the recessed non-contact regions have depths of about 0.01 to about 0.1 mm.

12. The guidewire of claim 1 wherein the recessed non-contact regions have depths of about 0.025 to about 0.075 mm.

13. The guidewire of claim 1 wherein the intermediate sheath has a proximal portion with an outer diameter approximately the same as the outer diameter of the proximal core section.

14. The guidewire of claim 1 wherein the intermediate sheath has a distal portion with an outer diameter approximately the same as the outer diameter of the flexible tubular member.

15. The guidewire of claim 1 wherein the intermediate sheath is about 4 to about 38 cm in length.

16. The guidewire of claim 1 wherein the intermediate sheath is about 6 to about 20 cm in length.

* * * * *